(12) United States Patent
Miles et al.

(10) Patent No.: US 9,980,829 B2
(45) Date of Patent: May 29, 2018

(54) METHOD, GUIDE, GUIDE INDICIA GENERATION MEANS, COMPUTER READABLE STORAGE MEDIUM, REFERENCE MARKER AND IMPACTOR FOR ALIGNING AN IMPLANT

(71) Applicant: Optimized Ortho Pty Ltd, New South Wales (AU)

(72) Inventors: Brad Peter Miles, Crows Nest (AU); Peter Bede O'Connor, Crows Nest (AU); Justin Roe, Crows Nest (AU); Brett Fritsch, Crows Nest (AU); Len Walter, Crows Nest (AU); Ed Marel, Crows Nest (AU); Michael Solomon, Crows Nest (AU); Brian Cheung, Crows Nest (AU); Milton Scott Bergeon, Crows Nest (AU); James William Pierrepont, Crows Nest (AU)

(73) Assignee: Corin Limited, Cirencester (GB)

( * ) Notice: Subject to any disclaimer, the term of this patent is extended or adjusted under 35 U.S.C. 154(b) by 580 days.

(21) Appl. No.: 14/405,742

(22) PCT Filed: Oct. 3, 2012

(86) PCT No.: PCT/AU2012/001198
§ 371 (c)(1),
(2) Date: Dec. 4, 2014

(87) PCT Pub. No.: WO2013/181684
PCT Pub. Date: Dec. 12, 2013

(65) Prior Publication Data
US 2015/0164657 A1    Jun. 18, 2015

(30) Foreign Application Priority Data
Jun. 5, 2012  (AU) ................................ 2012902337

(51) Int. Cl.
*A61F 2/46* (2006.01)
*G06F 19/00* (2018.01)
(Continued)

(52) U.S. Cl.
CPC ............ *A61F 2/4609* (2013.01); *A61B 90/13* (2016.02); *G16H 50/50* (2018.01);
(Continued)

(58) Field of Classification Search
CPC ....... A61F 2/46; A61F 2/4609; G06F 19/3437
See application file for complete search history.

(56) References Cited

U.S. PATENT DOCUMENTS

2004/0210233 A1* 10/2004 Yoon ..................... A61F 2/4609
                                                              606/102
2008/0312659 A1* 12/2008 Metzger ............... A61B 17/154
                                                              606/87
(Continued)

FOREIGN PATENT DOCUMENTS

JP    A2004237100    8/2004
JP    A2005137904    6/2005
(Continued)

OTHER PUBLICATIONS

European Search Report.
Japan Examination Report.
Australian Examination Rep.

*Primary Examiner* — Christopher Beccia
(74) *Attorney, Agent, or Firm* — Culhane Meadows PLLC; Robert C. Klinger

(57) ABSTRACT

There is provided a method (100) for aligning and positioning an implant (305). The method (100) comprises creating a reference using a guide (500) configured in accordance with patient specific data; fixing the reference using a reference marker (920) and delivering the implant (305) with an impactor (1005) aligned in accordance with the (Continued)

reference. Guide light emission means (515*a*) may be employed to create the reference, reference marker light emission means (515*b*) may be employed to fix the reference and impactor light emission means (515*c*) may be employed to align an impactor (1005).

44 Claims, 11 Drawing Sheets

(51) Int. Cl.
    *A61B 90/13*      (2016.01)
    *A61F 2/30*      (2006.01)
    *A61B 34/10*      (2016.01)
    *A61B 90/00*      (2016.01)

(52) U.S. Cl.
    CPC ... *A61B 2034/102* (2016.02); *A61B 2034/105* (2016.02); *A61B 2090/3945* (2016.02); *A61F 2/30942* (2013.01); *A61F 2002/4687* (2013.01)

(56) References Cited

U.S. PATENT DOCUMENTS

2011/0313424 A1* 12/2011 Bono .................. A61B 17/1746
                                                                         606/91

2012/0265208 A1* 10/2012 Smith ................. A61B 17/1626
                                                                         606/87
2013/0158557 A1* 6/2013 Komistek .............. A61B 17/15
                                                                         606/89

FOREIGN PATENT DOCUMENTS

| | | |
|---|---|---|
| JP | A2005525868 | 9/2005 |
| JP | A2007508050 | 4/2007 |
| JP | A2008515601 | 5/2008 |
| JP | A2011502626 | 1/2011 |
| JP | B4943419 B | 5/2012 |
| JP | A2012525890 | 10/2012 |
| WO | WO9959487 A1 | 11/1999 |
| WO | WO2011080260 A1 | 7/2011 |
| WO | WO2012021858 A2 | 2/2012 |
| WO | WO2012024271 A2 | 2/2012 |
| WO | WO2012113030 A1 | 8/2012 |
| WO | WO2012154914 A1 | 11/2012 |
| WO | WO2011065378 A1 | 4/2013 |

* cited by examiner

METHOD, GUIDE, GUIDE INDICIA GENERATION MEANS, COMPUTER READABLE STORAGE MEDIUM, REFERENCE MARKER AND IMPACTOR FOR ALIGNING AN IMPLANT

CROSS-REFERENCE TO RELATED APPLICATION(S)

The present application claims priority under 35 U.S.C. § 365 to International Patent Application No. PCT/AU2012/001198 filed Oct. 3, 2012, entitled "A METHOD, GUIDE, GUIDE INDICIA GENERATION MEANS, COMPUTER READABLE STORAGE MEDIUM, REFERENCE MARKER AND IMPACTOR FOR ALIGNING AN IMPLANT". International Patent Application No. PCT/AU2012/001198 claims priority under 35 U.S.C. § 365 and/or 35 U.S.C. § 119(e) to Australian Patent Application No. 2012902337 filed Jun. 5, 2012, which are incorporated herein by reference into the present disclosure as if fully set forth herein.

FIELD OF THE INVENTION

The present invention relates to orthopaedic implant technique and in particular to a method, guide, guide indicia generation means, computer readable storage medium, reference marker and impactor for aligning an implant.

The invention has been developed primarily for use in delivering an acetabulum implant cup and will be described hereinafter with reference to this application. However, it will be appreciated that the invention is not limited to this particular field of use and may be employed for delivering other implants.

This application is related to co-pending application PCT/AU2012/000179 entitled "A computer-implemented method, a computing device and a computer readable storage medium for providing alignment information data for the alignment of an orthopaedic implant for a joint of a patient" by the Applicant of the present Application, of which the entire contents are incorporated by reference.

BACKGROUND

According to existing arrangements, implants are aligned in accordance with standard models of the human body. For example, for a particular patient receiving an implant, implant variables may be selected from the standard model of the human body representing a Western male of 20 years in age being six-foot in height. However, implants delivered in this manner are not appropriate for patients deviating from the standard model which may result in the misalignment of the implant. Misaligned implants generally suffer from excessive wear and deterioration, requiring remedial surgery.

Furthermore, the post implant activities of patients differ greatly. For example, a first patient may engage in a substantial amount of walking while a second patient may engage in a substantial amount of skiing. However, implants delivered in accordance with existing arrangements fail to take into account desired post implant activities of patients.

Yet further, implants aligned in accordance with existing arrangements are subject to error during the delivery process. This problem is compounded by the confined spaces within which the surgeon must work. It is known that implants delivered by surgeons may vary in alignment by up to 15°. Again, and misaligned implant generally results in excessive wear and deterioration of the implant.

The present invention seeks to provide a method, guide, guide indicia generation means, computer readable storage medium, reference marker and impactor for aligning an implant, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY

According to one aspect, there is provided a method for aligning an implant, the method comprising creating a reference using a guide configured in accordance with patient specific data; and aligning the implant in accordance with the reference.

Advantageously, the method is adapted for aligning an implant suited for the specific requirements of a patient.

Preferably, the guide comprises a socket engaging portion and wherein the method further comprises engaging the socket engaging portion in a socket to align the guide.

Advantageously, the socket engaging portion is adapted for engaging the socket in a single orientation and rotation for the purposes of aligning the guide for creating the reference.

Preferably, the method further comprises manufacturing the socket engaging portion in accordance with the patient specific data.

Advantageously, the socket engaging portion is manufactured specifically for use by the patient during surgery.

Preferably, the method further comprises manufacturing the socket engaging portion in accordance with alignment data.

Advantageously, the socket engaging portion is adapted for aligning the guide in accordance with a selected alignment.

Preferably, the method further comprises manufacturing the socket engaging portion in accordance with geometric features of the socket.

Advantageously, the socket engaging portion is adapted for engaging the geometric features of the socket in a single inclination and orientation so as to allow for the correct alignment of the guide.

Preferably, the method further comprises manufacturing the socket engaging portion to engage an inner surface of the socket.

Preferably, the method further comprises manufacturing the socket engaging portion to engage a rim of the socket.

Advantageously, the socket engaging portion is adapted to conform not only to the geometric features within the socket but also those along the rim so as to provide a secure engagement with the socket.

Preferably, the socket engaging portion comprises a guide indicia generation means for generating a guide indicia and wherein the method further comprises aligning the guide with reference to the socket using the guide indicia generation means.

Advantageously, the guide indicia generation means allows for reuse of the socket engaging portion wherein the guide indicia generation means is configured according to a specific patient so as to guide the surgeon as to the correct alignment of the guide.

Preferably, the method further comprises selecting the guide indicia generation means from a set of guide indicia generation means of differing dimensions in accordance with a dimension of the socket.

Advantageously, there are provided a plurality of guide indicia generation means of differing sizes so as to allow for a surgeon to select from the plurality of guide indicia generation means the most suitably sized guide indicia generation means for the particular socket of the patient.

Preferably, the guide indicia generation means further comprises a guide indicia display device adapted to display the guide indicia.

Advantageously, the guide indicia display device is adapted to display the guide indicia on a surface of the guide indicia generation means so as to indicate to the surgeon the correct alignment of the guide.

Preferably, the method further comprises configuring the guide indicia display device in accordance with configuration data.

Preferably, the configuration data comprises alignment data.

Advantageously, the guide indicia display device is adapted to display and indicia for use by the surgeon for aligning the guide.

Preferably, the alignment data comprises inclination and anteversion angle data.

Preferably, the configuration data comprises a geometric feature of the socket.

Advantageously, the guide indicia display device is adapted for displaying an indicia for use by the surgeon in orientate in the guide with reference to the geometric features of the socket.

Preferably, the geometric feature is a rim of the socket.

Preferably, the guide indicia display device comprises a plurality of light modules.

Preferably, the guide indicia generation means is adapted to display the guide indicia on a surface of the guide indicia generation means using the plurality of light models.

Preferably, the guide indicia is a circumferential contour.

Preferably, the method further comprises aligning the circumferential contour with a rim of the socket.

Preferably, the method further comprises transmitting the configuration data to the guide indicia generation means.

Preferably, the method further comprises wirelessly transmitting the configuration data to the guide indicia generation means.

Advantageously, the configuration data may be calculated at a remote computer device and provided across the air to the guide indicia generation means. In this manner, the processing of the configuration data may be done at a remote location away from the operating theatre. Furthermore, the wireless provision of the configuration data to the guide indicia generation means does not compromise the sterility of the guide as compared to a contact data interface.

Preferably, the method further comprises calculating optimal alignment data in accordance with the patient specific data.

Advantageously, the alignment data may be calculate in accordance with the patient specific characteristics such as biomechanical confederation and the patient needs such as desired post implant activity.

Preferably, the method further comprises calculating candidate alignment data in accordance with the patient specific data and selecting the optimal alignment data from the candidate alignment data.

Preferably, the method further comprises calculating the candidate alignment data in accordance with patient data and selecting the optimal alignment data in accordance with at least one desired post implant activity.

Advantageously, the selection of the optimal alignment data in accordance with the at least one desired post implant activity allows for the selection of alignment data that will substantially reduce excessive wear of the implant.

Preferably, the patient data comprises dynamic characteristic data representing at least one dynamic characteristic.

Preferably, the method further comprises calculating the dynamic characteristic data from imaging data obtained from an imaging technique selected from the set of imaging techniques comprising CT and radiograph imaging techniques.

Preferably, the method further comprises capturing the image data from a patient during at least one functional activity.

Preferably, the dynamic characteristics data comprises dynamic characteristic data selected from the set of characteristic data comprising lumber cobb angle, sacreal slope and anterior pelvic plane characteristic data.

Preferably, the method further comprises calculating the dynamic characteristic data in accordance with a virtual model.

Preferably, calculating candidate alignment data comprises simulating at least one functional activity.

Advantageously, the simulation allows for the variation of one or more implant variables (such as the alignment of an implant) for the subsequent a selection of the most appropriate implant variables in accordance with the patient's desired post implant activities.

Preferably, calculating candidate alignment data further comprises simulating at least one alignment of the implant.

Preferably, the method further comprises employing a rigid body dynamic physics simulation.

Preferably, calculating candidate alignment data comprises calculating at least one joint reaction vector from a simulation of a functional activity.

Preferably, the method further comprises selecting the optimal alignment data in accordance the at least one joint reaction vector.

Advantageously, the joint reaction vector may be indicative of the misalignment of an implant which would result in the excessive wear of the implant.

Preferably, the method further comprises selecting the optimal alignment data in accordance with a desired post implant activity.

Preferably, the guide comprises guide light emission means, and wherein creating the reference comprises creating the reference using the guide light emission means.

Preferably, creating the reference comprises projecting a guide reference light beam from the guide light emission means onto a surface and noting the location of the light beam on the surface.

Advantageously, the guide is used to create a reference using the guide reference light beam so as to allow for the subsequent removal of the guide and the insertion of the implant in accordance with the reference. Furthermore, the projection of the guide reference light beam onto a distance surface such as the ceiling or wall of an operating theatre allows for accurate alignment of the implant within a reference area of about 30 cm in radius.

Preferably, the guide light emission means is detachable.

Advantageously, the guide light emission means may be employed for use by other devices described herein including the reference market and the impactor.

Preferably, the guide reference light beam is a laser.

Advantageously, the laser allows for a highly visible and accurate reference point.

Preferably, the guide light emission means is adapted to emit a second guide reference light beam.

Preferably, the method further comprises fixing the reference using a reference marker.

Advantageously, the reference marker is used for fixing the reference so as to allow for the removal of the guide and the subsequent insertion of the implant in accordance with the reference.

Preferably, fixing the reference comprising aligning the reference marker in accordance with the reference.

Preferably, the method further comprises fastening the reference marker to a patient.

Preferably, fastening the reference marker to the patient comprises fastening the reference marker to a bone of the patient.

Preferably, the bone is the pelvis bone.

Advantageously, by fastening the reference marker to the patient, the reference point becomes immune to movement by the patient such as where the position of the patient is shifted during the operation.

Preferably, the guide comprises a drill guide and wherein fixing the reference comprises drilling a drill hole using the drill guide and inserting at least a portion of the reference marker into the drill hole.

Advantageously, the drill guide may be employed for the purposes of physically aligning the reference marker with the guide. In this manner, no guide light emission means is required.

Preferably, the reference marker comprises a joint, and wherein fixing the reference comprises configuring the joint to align the reference marker in accordance with the reference.

Preferably, the joint is a poly axial joint.

Advantageously, the joint allows for the initial fastening of the reference marker to the patient and the subsequent alignment of the reference marker light beam in accordance with the reference.

Preferably, the reference marker comprises a reference marker light emission means.

Preferably, the reference marker light emission means is adapted to emit a reference marker light beam and wherein fixing the reference comprises aligning the reference marker light beam and the reference.

Preferably, the reference marker light emission means is detachable.

Preferably, the reference marker light beam is a laser.

Preferably, aligning the implant comprises delivering the implant into a socket with an impactor aligned in accordance with the reference.

Advantageously, the implant is delivered in alignment with the reference.

Preferably, the method further comprises reaming the socket prior to delivering the implant.

Preferably, the impactor is adapted to engage the reference marker.

Preferably, the impactor comprises a sheath for engaging the reference marker.

Preferably, the impactor comprises an impactor light emission means adapted for emitting an impactor light beam and wherein aligning the impactor comprises aligning the impactor light beam and the reference.

Advantageously, the impactor light emission means that allows for the alignment of the impactor in accordance with the reference created by the guide so as to allow for the accurate alignment of the implant.

Preferably, the impactor light beam is a laser.

According to another aspect, there is provided a guide for aligning an implant, wherein the guide comprises a socket engaging portion configured in accordance with patient specific data and wherein the socket engaging portion is adapted for aligning the guide.

Preferably, the socket engaging portion is manufactured in accordance with patient specific data.

Preferably, the socket engaging portion is manufactured in accordance with alignment data.

Preferably, the socket engaging portion is manufactured in accordance with geometric features of a socket.

Preferably, the socket engaging portion is adapted to engage an inner surface of the socket.

Preferably, the socket engaging portion is adapted to engage a rim of a socket

Preferably, the socket engaging portion comprises a guide indicia generation means for generating a guide indicia for aligning the guide.

Preferably, the guide indicia generation means further comprises a guide indicia display device adapted to display the guide indicia.

Preferably, the guide indicia display device is configured in accordance with configuration data.

Preferably, the configuration data comprises alignment data.

Preferably, the alignment data comprises inclination and anteversion angle data.

Preferably, the configuration data comprises a geometric feature of the socket.

Preferably, the geometric feature is a rim of the socket.

Preferably, the guide indicia display device comprises a plurality of light modules.

Preferably, the guide indicia generation means is adapted to display the guide indicia on a surface of the guide indicia generation means using the plurality of light models.

Preferably, the guide indicia is a circumferential contour.

Preferably, wherein the circumferential contour is adapted for aligning with a rim of a socket.

Preferably, the guide indicia generation means comprises a receiver module adapted for receiving the configuration data.

Preferably, the receiver module is a wireless receiver module.

According to another aspect, there is provided a guide indicia generation means for generating a guide indicia for aligning a guide, the guide indicia generation means comprising a processor for processing digital data; a memory device for storing digital data including computer program code and being coupled to the processor; and a guide indicia display device for displaying the guide indicia and being coupled to the processor, wherein the processor is controlled by the computer program code to display, using the guide indicia display device, the guide indicia in accordance with configuration data.

Preferably, the configuration data comprises alignment data.

Preferably, the alignment data comprises inclination and anteversion angle data.

Preferably, the configuration data comprises a geometric feature of the socket.

Preferably, the geometric feature is a rim of the socket.

Preferably, the guide indicia display device comprises a plurality of light modules.

Preferably, the guide indicia display device is a circumferential display device adapted to display the guide indicia on a circumferential surface of the guide indicia generation means.

Preferably, the guide indicia generation means further comprises a data interface for receiving data from a data network and being coupled to the processor, wherein the processor is further controlled by the computer program code to receive, via the data interface, the configuration data.

Preferably, the data interface is a wireless data interface.

Preferably, the processor is further controlled by the computer program code to store, in the memory device, the configuration data.

According to another aspect, there is provided a computer readable storage medium comprising computer program code instructions for generating a guide indicia for aligning a guide, the computer program code instructions comprising instructions for displaying, using a guide indicia display device, the guide indicia in accordance with configuration data.

Preferably, the configuration data comprises alignment data.

Preferably, the alignment data comprises inclination and anteversion angle data.

Preferably, the configuration data comprises a geometric feature of the socket.

Preferably, the geometric feature is a rim of the socket.

Preferably, the guide indicia display device comprises a plurality of light modules.

Preferably, the guide indicia display device is a circumferential display device.

Preferably, the computer readable storage further comprises instructions for receiving, via a data interface, the configuration data.

Preferably, the data interface is a wireless data interface.

Preferably, the computer readable storage medium further comprises instructions for storing, in the memory device the configuration data.

According to another aspect, there is provided a reference marker for fixing a reference created by a guide as described herein for aligning an implant.

Preferably, the reference marker is adapted for alignment in accordance with the reference.

Preferably, the reference marker is adapted for fastening to a patient.

Preferably, the reference marker is adapted for fastening to a bone of the patient Preferably, the bone is the pelvis bone.

Preferably, the reference marker comprises a reference pin adapted for insertion into a drill hole.

Preferably, the reference marker further comprises a joint adapted for aligning the reference marker in accordance with the reference.

Preferably, the joint is a poly axial joint.

Preferably, the reference marker comprises a reference marker light emission means.

Preferably, reference the marker light emission means is adapted to emit a reference marker light beam adapted for alignment with the reference.

Preferably, the reference marker light emission means is detachable.

Preferably, the reference marker light beam is a laser.

According to another aspect, there is provided an impactor for aligning an implant into a socket in alignment with a reference fixed by a reference marker as described herein.

Preferably, the impactor is adapted to engage the reference marker.

Preferably, the impactor comprises a sheath for engaging the reference marker.

Preferably, the impactor comprises an impactor light emission means adapted for emitting an impactor light beam adapted for alignment with the reference.

Preferably, the impactor light beam is a laser.

Other aspects of the invention are also disclosed.

BRIEF DESCRIPTION OF THE DRAWINGS

Notwithstanding any other forms which may fall within the scope of the present invention, a preferred embodiments of the invention will now be described, by way of example only, with reference to the accompanying drawings in which.

DESCRIPTION OF EMBODIMENTS

Figure 1:
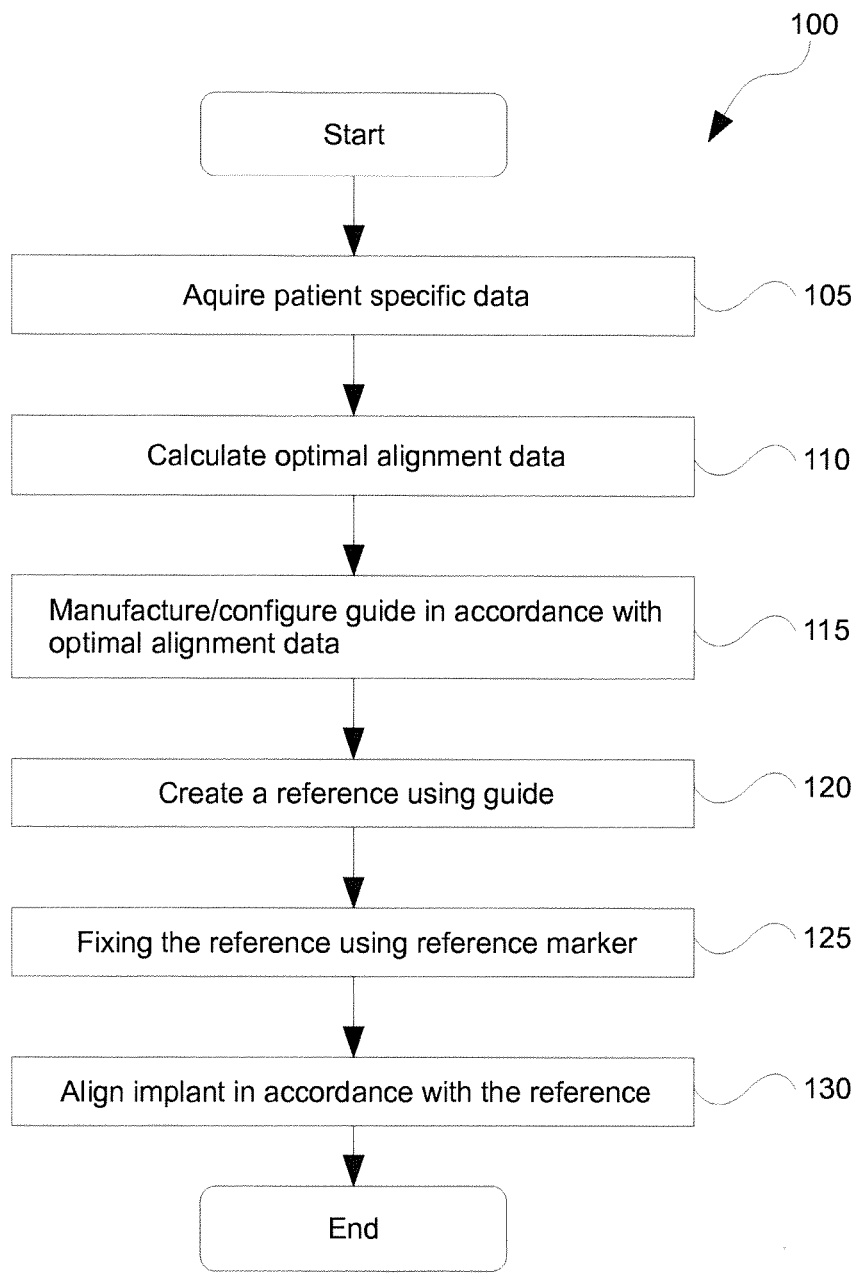
FIG. 1 shows a method for aligning an implant in accordance with a preferred embodiment of the present invention.

It should be noted in the following description that like or the same reference numerals in different embodiments denote the same or similar features.

A Method For Aligning An Implant

Referring to FIG. 1, there is provided a method 100 for aligning an implant during surgery. Specifically, the method 100 comprises creating a reference using a guide configured in accordance with patient specific data, fixing the reference using a reference marker so as to allow for the removal of the guide and thereafter, aligning the implant in accordance with the reference.

As will become apparent from the description herein, the method 100 employs a guide 500 having a socket engaging portion 505 adapted for engagement with a socket so as to align the guide 500 for the purposes of creating a reference for the subsequent delivery of the implant. Furthermore, the method 100 employs a reference marker 920 for the purposes of fixing the reference allowing for the removal of the guide 500 and the subsequent insertion of the implant cup 305 using an impactor 1005 aligned in accordance with the reference which has been fixed by the reference marker 920.

Figure 5:
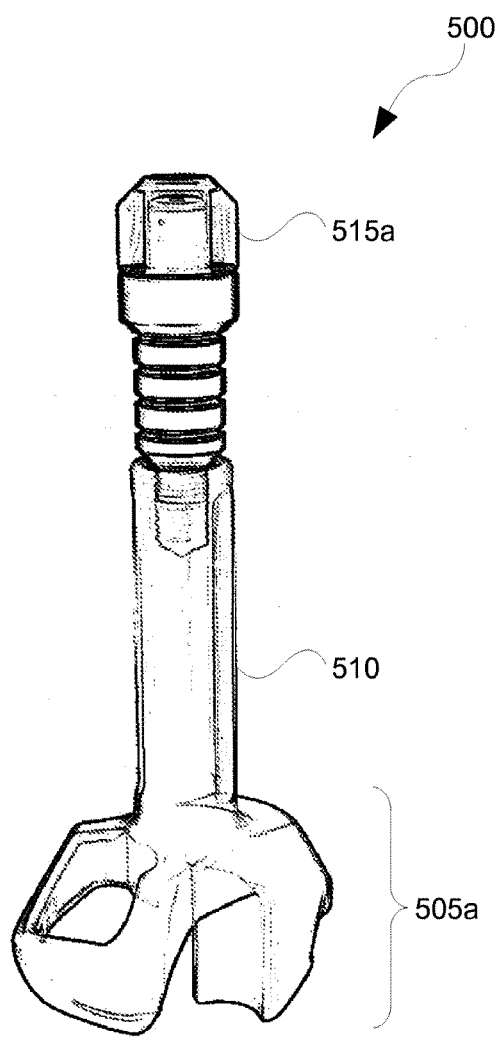
FIG. 5 shows a guide having a socket engaging portion manufactured in accordance with patient specific data in accordance with a preferred embodiment of the present invention.
Figure 8:
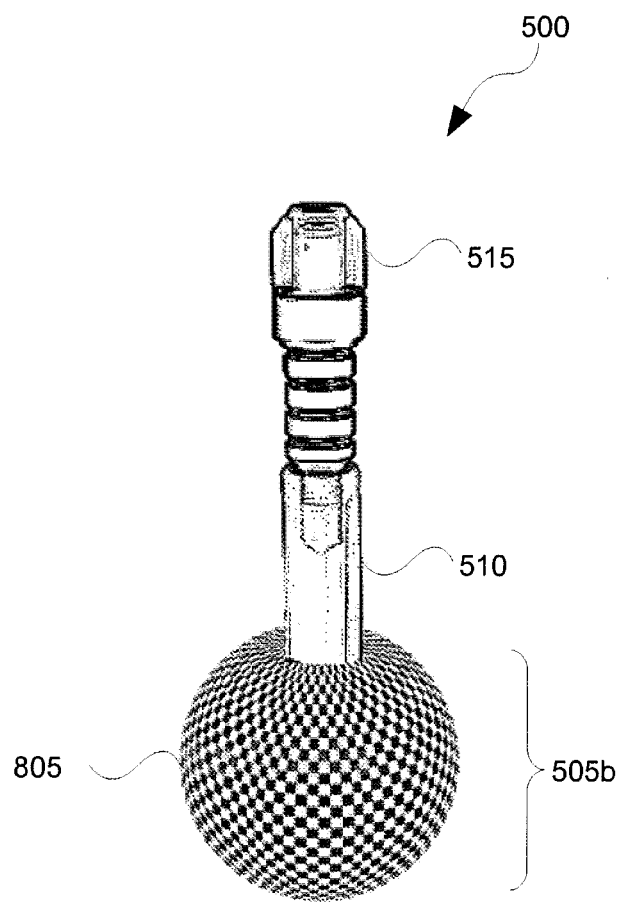
FIG. 8 shows a socket engaging portion of the guide of FIG. 5 having a guide indicia generation means in accordance with another preferred embodiment of the present invention.

Specifically, referring to FIG. 5, there is shown a guide 500 having a socket engaging portion 505a in accordance with a first embodiment, and referring to FIG. 8, there is shown the guide 500 having a socket engaging portion 505b in accordance with a second embodiment. As will become apparent from the description herein, the socket engaging portion 505 is configured or manufactured in accordance with optimal alignment data and geometric feature data calculated from patient specific data, such that the implant 305 can be aligned accurately in accordance with the optimal alignment data.

The embodiments herein are described with reference to hip replacements and in particular to delivering an implant cup 305 into an acetabulum of a patient. However, it should be noted that the embodiments are equally applicable to other types of implants.

Calculating Optimal Alignment Data in Accordance with Patient Specific Data

Referring to FIG. 1, the method 100 starts at step 105 where patient specific information is acquired from a patient for the purposes of calculating patient specific data so as to allow for the computation of an optimal alignment for the implant 305.

Figure 2:
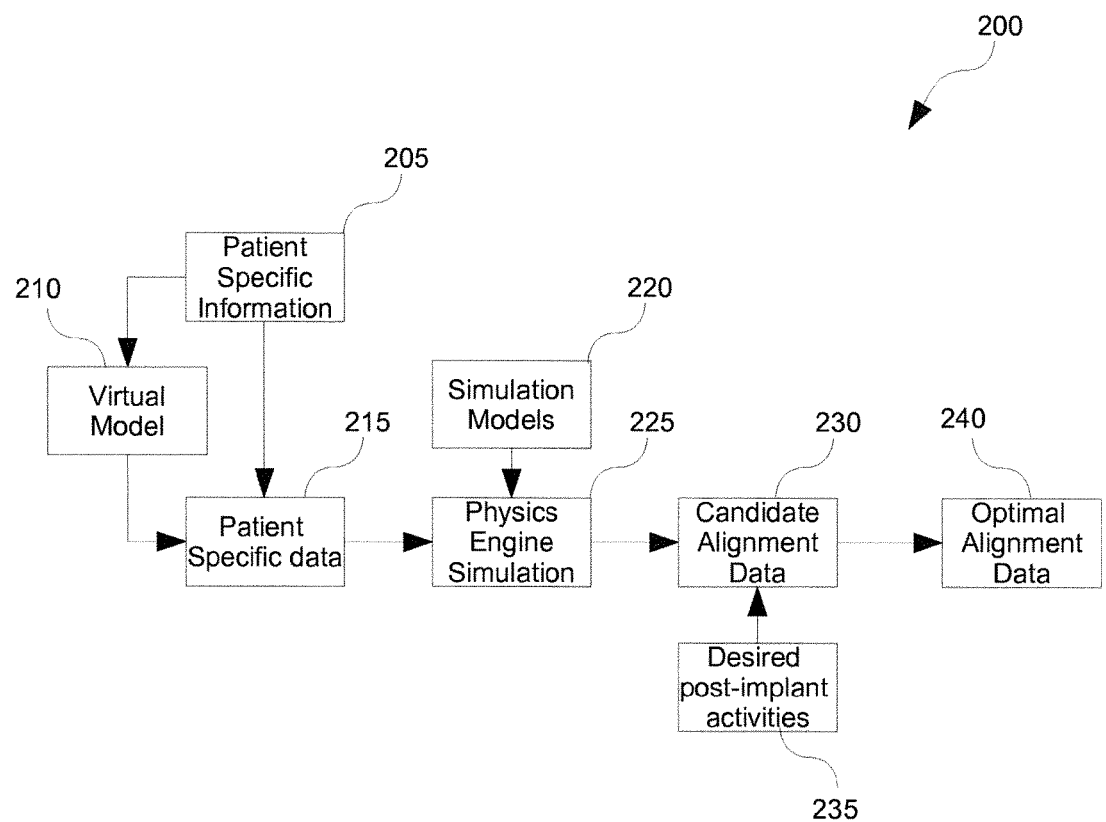
FIG. 2 shows a method for calculating optimal alignment data using a physics engine simulation in accordance with a preferred embodiment of the present invention.

Referring now to FIG. 2, there is shown a method 200 for calculating optimal alignment data in accordance with patient specific information and at least one desired post implant activity. It should be noted that the message to hundreds maybe adapted for completing other in addition to or alternatively to alignment data (inclination and anteversion), such as optimal position data of the implant which may comprise the depth of the implant 305 in a socket, which, where the socket is an acetabulum may represent whole medial that implant cup 305 is sunk into the acetabulum.

Figure 3:
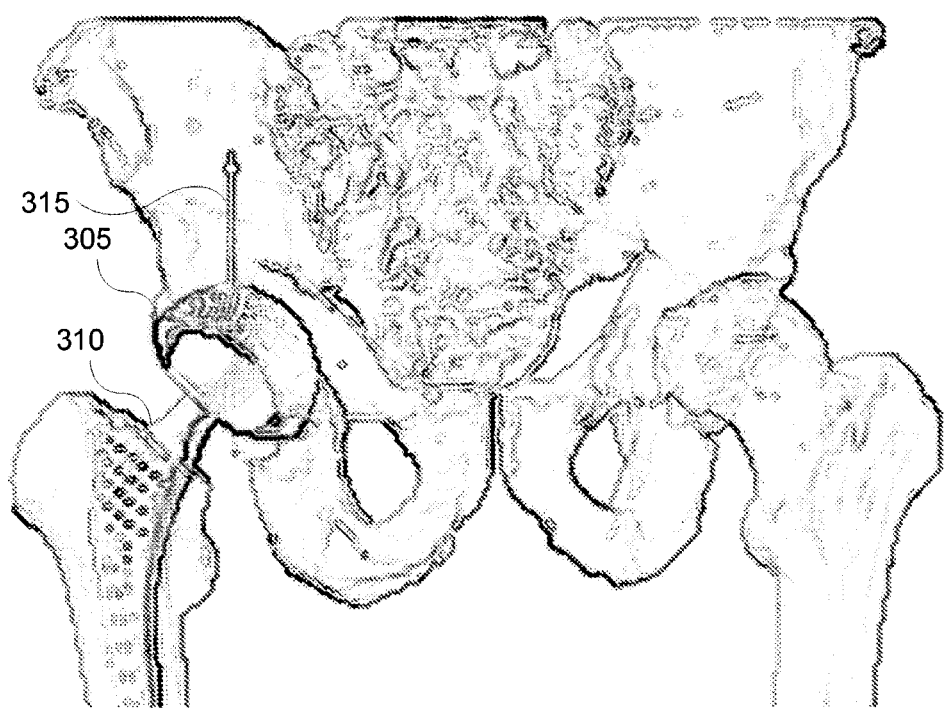
FIG. 3 shows a joint reaction vector which had been calculated using the physics engine simulation of FIG. 2 in accordance with another embodiment of the present invention.

The method 200 starts at step 205 where patient specific information is gathered from the patient. The patient specific information may be gathered in a number of ways such as observation, survey and the like. In a preferred embodiment, the patient specific information is captured from the patient using imaging techniques such as CT scan, standard radiograph and the like. Images from the CT scan are used for determining necessary biomechanical landmarks for the purposes of aligning and orientating the implant for use in the physics engine simulation (described below). Specifically, referring to FIG. 3 there is shown the pelvis of the patient wherein the implant cup 305 and the implant head 310 have been aligned and orientated with reference to the pelvis and femur of the patient for use in the physics engine simulation described below.

The patient specific information may include spinal and pelvic variables such as sacral slope, anterior pelvic plane, lumbar cobb angle and the like.

The patient specific information may be supplemented by dynamic characteristics representing at least one dynamic characteristic of the patient. A radiograph may be employed for calculating these dynamic characteristics by imaging the patient during various functional activities such as walking, standing up, sitting down and the like. Furthermore, at step 210 of method 200, a virtual model may be employed for calculating additional dynamic characteristic data for the patient.

At step 215 of the method 200, patient specific data is calculated from the patient specific information for the purposes of input into the physics engine simulation described at step 225.

The physics engine simulation 225 employs rigid body dynamics to simulate various functional activities of the patient. These functional activities stimulated by the physics engine simulation 225 may be the same or different functional activities as those conducted during the patient specific information gathering process 205 as described above. For example, the method 200 may employ a database of simulation models shown at step 220 for use in simulating other functional activities of the patient.

During the simulation process, the physics engine selection 225 will vary various variables for each functional activity such as the alignment of the proposed implant 305. The alignment of the proposed implant 305 may be represented by inclination and anteversion angles. Other implant variables may be varied during the simulation in addition to the alignment of the proposed implant 305.

During the simulation process, one or more joint reaction vectors may be calculated for each implant variable set. As is described in further detail below, joint reaction vectors may be indicative of whether an implant will experience excessive wear if aligned in accordance with a set of variables. Specifically, referring to FIG. 3, there is shown a joint reaction vector 315 which has been calculated by the physics engine simulation 225 for a first implant variable set.

Joint Reaction Visualisation

Figure 4:
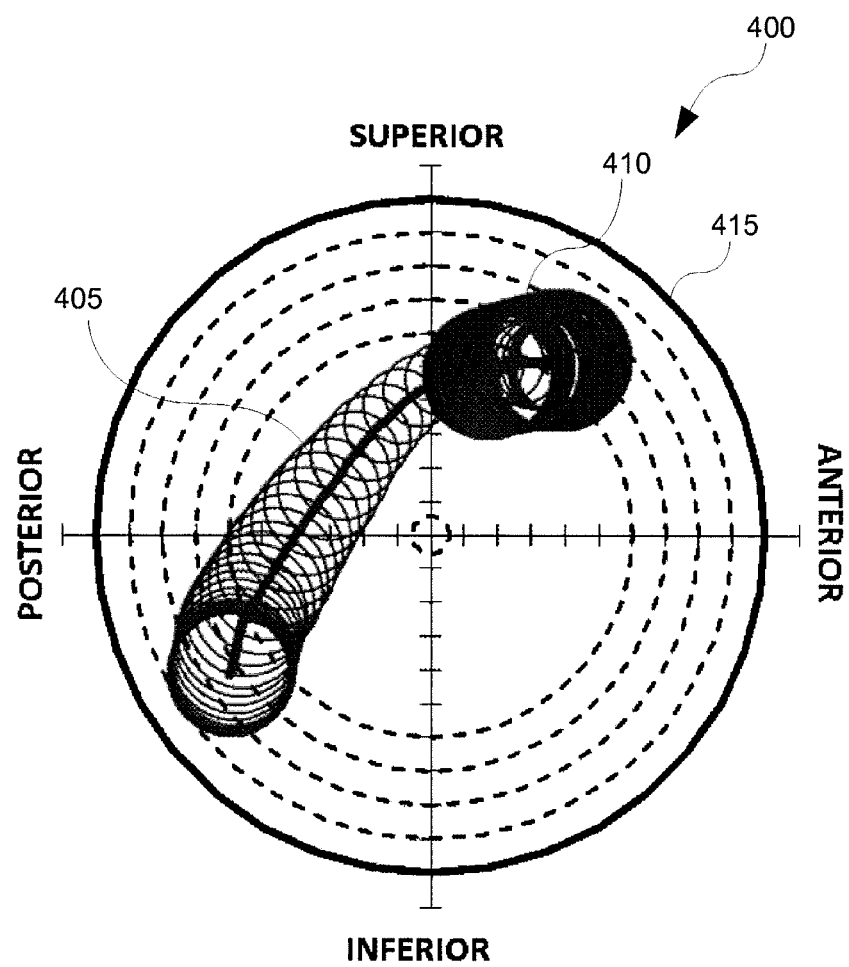
FIG. 4 shows a joint reaction visualisation showing various joint reaction vectors calculated by the physics engine simulation of FIG. 2 during various functional activities in accordance with differing implant variables in accordance with another embodiment of the present invention.

Referring to FIG. 4 there is shown a joint reaction visualisation 400 showing various joint reaction vectors calculated by the physics engine simulation 225 during various functional activities in accordance with differing implant variables.

The joint reaction visualisation 400 comprises a 2D hemisphere 415 representing the 3D implant cup, having a centroid surrounded by graduated degrees to the lateral edge of the hemisphere 415.

As will become apparent from below, the exemplary joint reaction visualisation 400 represents two joint reaction vectors calculated for two functional activities for a first implant variable set. For example, the joint reaction visualisation 400 may represent the joint reaction vectors calculated by the physics engine simulation 225 for an implant cup 305 orientated at a first inclination and anteversion angle. A further joint reaction visualisation 400 (not shown) may be generated by the physics engine simulation 225 for the same two functional activities for a second variable set. For example, were the physics engine simulation 225 to alter the inclination angle of the implant cup 305, the position of the joint reaction vectors would lie in a differing position.

An optimal implant variables set will constrain joint reaction vectors substantially within the centre of the implant cup 305 and avoid situations where the joint reaction vectors stray towards the edges of the implant cup 305. An implant configured in this way will exhibit lesser wear and deterioration as opposed to an implant experiencing laterally directed joint reaction vectors as a result of the misalignment. As will be described in further detail below, the physics engine simulation 225 generates various joint reaction visualisation 400 in accordance with implant variables variations such that the surgeon (or a computer implemented algorithm) selects the optimal implant variable set indicated by the visualisation 400 exhibiting the most centralised joint reaction vectors.

In the embodiment given in FIG. 4, the joint reaction visualisation 400 comprises two exemplary joint reaction vectors. The first joint reaction vector visualisation 405 represents a sit to stand functional activity joint reaction vector and comprises a trajectory across the hemisphere 415 indicative of the joint reaction force that would bear against the implant cup 405 during the functional activity as calculated by the physics engine simulation 225. The trajectory of the joint reaction force is indicated by the solid central line of the joint reaction vector visualisation 405. However, not only is the location of the joint reaction force important, but also the magnitude of the force. For example, while the trajectory may indicate that the joint reaction vector is substantially constrained within the centre of the hemisphere 415 it may not be readily apparent to the surgeon that the magnitude of the force may expand the contact surface of the implant head against the implant cup 405 beyond the lateral edges of the hemisphere 415. As such, the joint reaction vector visualisation 405 also comprises concentric rings about the trajectory having a radius indicative of the contact surface of the implant head and the implant cup 405 in accordance with the magnitude of the joint reaction force. As is apparent from the exemplary joint reaction vector visualisation 405, the magnitude of the force of the joint reaction vector varies along the trajectory. The contact surface of the implant head and implant cup 405 may be calculated using an appropriate contact mechanics calculation including the Hertzian theory of non-adhesive elastic contact.

The exemplary joint reaction visualisation 400 comprises a second exemplary joint reaction vector visualisation 410, which, may for example, represent the joint reaction vectors during a walking functional activity. As is apparent from the embodiment given, the second exemplary joint reaction vector visualisation 410 shows force being directed towards the lateral edges of the implant cup 405 which may be indicative of excessive or uneven wear of the implant cup 405 should be implant cup 405 be aligned in this manner.

As alluded to above, in one embodiment, the physics engine some simulation 225 may employ various predetermined simulation models 220 for the purposes of simulating further functional activities. For example, simulation models 220 may comprise a simulation of a stair climb functional activity.

At step 230 of method 200, candidate implant variable sets are output by the physics engine simulation 225, each accompanied by the respective joint reaction vector visualisation 400. For example, each of the candidate implant variables may comprise a unique inclination and anteversion angle representing the alignment of the implant cup.

Now, from the two or more candidate variables output by the physics engine selection 225 an optimal variable set is selected in accordance with desired post implant activities. For example, where the patient indicates that the patient intends engaging in substantial walking activity, while hardly ever engaging in a stair climbing activity, the surgeon (or a computer algorithm) may select the implant variable set corresponding to the joint reaction visualisation showing the walking joint reaction vector visualisation 410 most centered with and be hemisphere 415.

Socket Engaging Portion

Having selected an optimal implant variable set (indicative of the alignment of the implant and other implant parameters) in accordance with the patient specific data, the method 100 progresses to step 115 where the socket engaging portion 505 is manufactured or configured in accordance with configuration data representative of the optimal implant variable set (and optimal implant position variable set in certain embodiments such as the medial depth of the implant cup 305 within the socket) and other patient specific data including the geometry of the socket.

Referring to the first embodiment of the socket engaging portion 505a as substantially shown in FIG. 5, the socket engaging portion 505a is manufactured in accordance with the configuration data. As is apparent from the description herein, the socket engaging portion 505a is adapted for engaging a socket of a patient so as to align the guide 500 in accordance with the optimal implant variable set. For example, during surgery, the surgeon, holding the guide 500 by the shaft 510, will insert the guide 500 into a wound of the patient such that the socket engaging portion 505a correctly engages a socket of the patient. As will be described in further detail below, the socket engaging portion 505a is manufactured in accordance with these specific geometric features of the socket of the patient such that the socket engaging portion 505a will only engage the socket at a particular orientation. Once the socket engaging portion 505a has correctly engaged the socket of the patient, and as will be further described below, the surgeon will use the guide to create the reference for the subsequent insertion of the implant cup 305.

Figure 6:
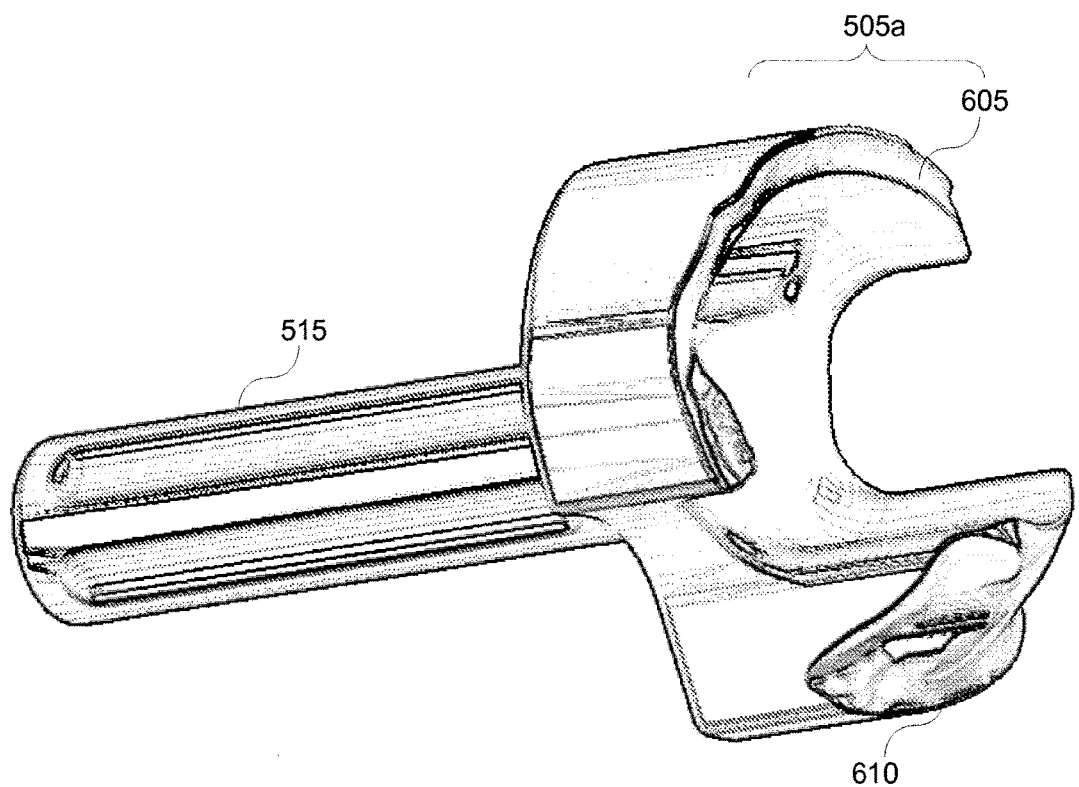
FIG. 6 shows a bottom view of the socket engaging portion of the guide of FIG. 5 in further detail in accordance with another embodiment of the present invention.

Referring now to FIG. 6, there is shown a bottom view of the guide 500 showing the socket engaging portion 505a in further detail. As is apparent from this embodiment, the socket engaging portion 505a is shaped to conform to the geometry of the socket of the patient such that the shaft 510 is aligned correctly in accordance with the optimal alignment data calculated from the patient specific data. As alluded to above, the geometry of the socket of the patient is ascertained at step 105 of method 100 by CT scan or the like. There are differing manners by which the socket engaging portion 505a may be shaped and configured so as to correctly engaged to the geometric features of the socket of the patient. In the embodiment given in FIG. 6, the socket engaging portion 505a comprises a rim engaging surface 605 adapted to bear downwardly on a rim of the socket and an inner surface engaging surface 610 adapted to bear against an inner surface of the socket.

Figure 7:
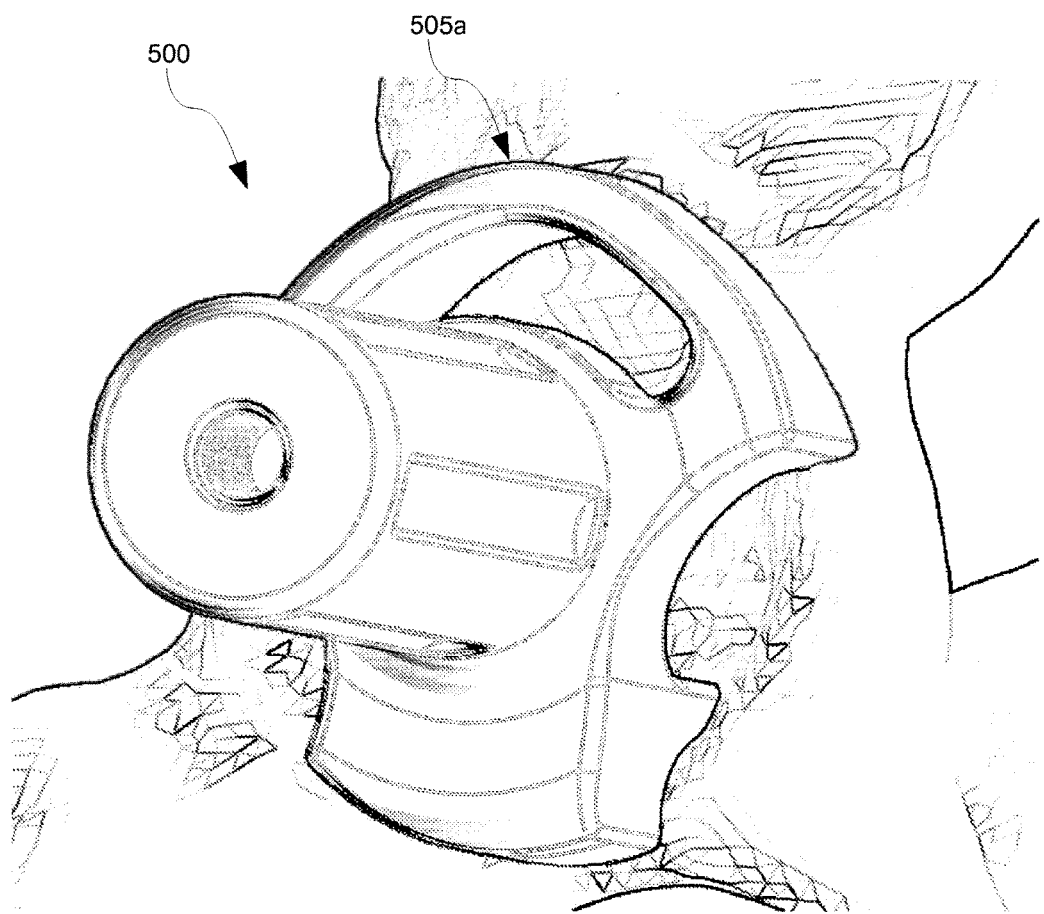
FIG. 7 shows the socket engaging portion of the guide of FIG. 5 engaged in an acetabulum socket in accordance with another embodiment of the present invention.

Referring to FIG. 7, there is shown the socket engaging portion 505a in situ, and in particular engaged by an acetabulum socket. As is readily apparent from the representation shown, the rim engaging surface 605 and the inner surface engaging surface 610 restrict the socket engaging portion 505a within the acetabulum in a particular orientation.

Preferably, the socket engaging portion 505a is manufactured using a rapid prototyping technique, such as an additive manufacturing process. In this manner, the socket engaging portion 505a may be manufactured within a short time period between the determination of the optimal alignment and the delivery of the implant during surgery. Generally, the guide 500 is manufactured for single use wherein the guide 500 is disposed of post surgery.

Turning now to be second embodiment of the socket engaging portion 505b as substantially shown in FIG. 8, as will become apparent from the description below, the socket engaging portion 505b is be adapted for reuse. Furthermore, the socket engaging portion 505b is designed in a generic manner so as to be adapted for use by different patients. In this manner, once the socket engaging portion 505*b* has been used during an operation, the socket engage important 505*b* may be sterilised and reused for a subsequent operation for a different patient.

Referring now to the socket engaging portion 505*b*, the socket engaging portion 505*b* comprises a guide indicia generation means 805 adapted to generate a guide indicia for use by the surgeon in ascertaining when the guide 500 is aligned correctly.

The guide indicia generation means 805 is adapted for configuration in accordance with configuration data including the geometric features of the socket of the patient and the optimal alignment of the guide 500.

It should be noted that the guide indicia generation means 805 may be provided in differing sizes so as to be accommodated by patients having sockets of varying sizes. In this manner, two or more guides 500 may be provided in a kit, each having a socket engaging portion 505*b* of varying dimension. In this manner, the surgeon is able to select the most appropriately sized socket engaging portion 505*b* for insertion into the acetabulum of the patient.

It should be noted that the socket engaging portion 505*b* may be detachable from the shaft 510 of the guide 500.

Figure 11:
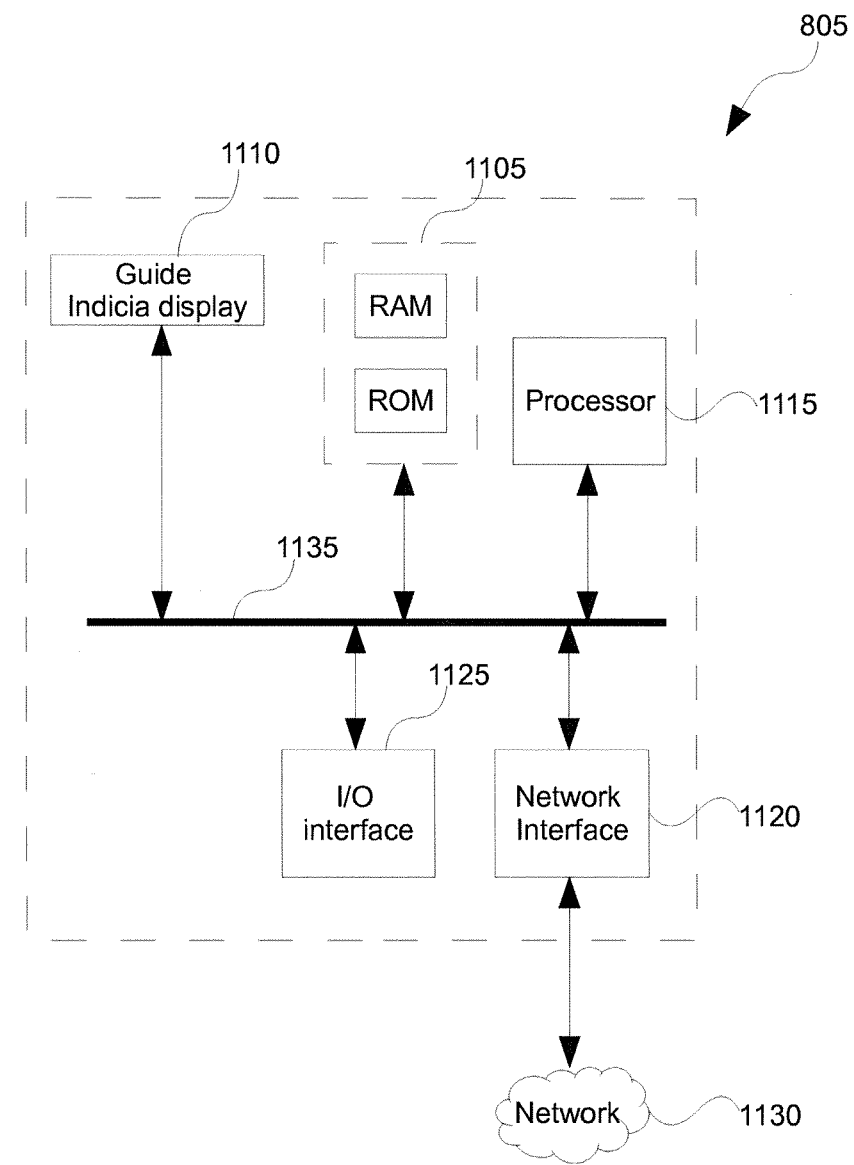
FIG. 11 shows an exemplary schematic of the components of the guide indicia generation means of FIG. 8 in accordance with another embodiment of the present invention.

Referring now to FIG. 11, there is shown an exemplary schematic of the components of the guide indicia generation means 805. In particular, the guide indicia generation means 805 comprises a guide indicia display device 1110 for the purposes of outputting guide indicia. The guide indicia are used by the surgeon during surgery to ascertain when the guide 500 is aligned correctly. There are differing manners by which the guide indicia may be provided by the guide indicia display device 1110.

In a first embodiment, the surface of the socket engaging portion 505*b* comprises a tactile sensor such as a plurality of capacitive sensors to ascertain the orientation and rotation of the socket engaging portion 505*b* within the socket. In this manner, when guide indicia generation means 805 ascertains from the tactile sensor that the socket engaging portion 505*b* is aligned correctly, the guide indicia generation means 805 may indicate the correct alignment, such as by illuminating a red light. Alternatively, the guide indicia generation means 805 may illuminate a red light when the guide 500 is incorrectly aligned and illuminate a green light when the guide 500 is aligned correctly.

In a second embodiment, the guide indicia generation means 805 is adapted to display a circumferential guide indicia (e.g. a contour adapted to conform with the rim of the socket) about the surface of the socket engaging portion 505*b* using the guide indicia display device 1110. In this embodiment, the circumferential guide indicia is used by the surgeon for alignment with the rim of the socket.

The guide indicia may be displayed by the guide indicia display device 1110 in a number of manners including liquid crystal display so as to display a black circumferential contour circumference the socket engaging portion 505. However, in a preferred embodiment, the guide indicia display device 1110 comprises a plurality of lights modules for greater visibility. In this manner, the guide indicia display device 1110 is adapted to selectively operate a subset of the lights modules for the purposes of illuminating the guide indicia on the surface of the guide indicia generation means 805.

In one embodiment, the lights modules may be provided by a number of LED lights spaced appropriately about the circumference of the guide indicia generation means 805. Note that the light modules need not reach substantially both the top and the bottom of the guide indicia generation means 805 as is given by the embodiment FIG. 8, but may rather be located to provide a band (such as a band of about 1 cm in width) about the circumference of the guide indicia generation means 805 so as to provide a tolerance to cater for different types of socket rims.

Of course, the guide indicia may be provided by other types of light emission means. For example, a flexible organic light emitting diode (OLED) device may be provided in cylindrical format so as to provide a circumference guide indicia. In other embodiments, a flat display matrix may be employed adjacent a reflector to convert the two-dimensional display of the display matrix to the circumferential surface of the guide indicia generation means 805. For example, the display matrix may be located adjacent a conical reflector wherein a pixel towards the centre of the display matrix will correspond with a lower location of the circumferential surface of the guide indicia generation means 805 and a pixel towards the outer edge of the display matrix will correspond with a high location of the circumferential surface of the guide indicia generation means 805.

The guide indicia generation means 805 further comprises a processor 1115 for processing digital data and a memory device 1105 for the purposes of storing digital data including computer program code and optimal alignment data.

Furthermore, the guide indicia generation means 805 may comprise a network interface 1120 (preferably a wireless network interface) for the purposes of sending and receiving data across a data network 1130. In this manner, the guide indicia generation means 805 may be provided with the configuration data prior to an operation.

In use, in order to create the guide indicia, the surgeon may select an appropriately sized guide indicia generation means 805 for insertion into the socket of a patient. The guide indicia generation means 805 may then be provided with the configuration data representing the geometric features of the socket and the optimal alignment data for the purposes of configuring the guide indicia display device 1110. There are a number of manners by which the optimal alignment data and may be provided to the guide indicia generation means 805.

In a preferred embodiment, the network interface 1120 is a wireless network interface such as an 802.11 or Bluetooth wireless network interface adapted for receiving the configuration data from a data network. In this manner, a remote computing device may be utilised for the purposes of calculating the configuration data, whereafter the identification of the guide indicia generation means 805 is input into the computing device such that the computing device may provision the configuration data across the wireless network to the guide indicia generation means 805.

Of course, there may be other means by which the optimal alignment data may be transmitted to the guide indicia generation means 805. For example, a docking station may be employed having an acoustic or optical data interface for the purposes of transmitting the data to the guide indicia generation means 805.

The guide indicia generation means 805 may further more comprise a rechargeable battery (not shown) to power the device during surgery. The rechargeable battery may be recharged via external contacts, but given the sterility requirements of an operating theatre, the guide indicia generation means 805 preferably comprises a watertight external cladding and wherein the rechargeable battery is recharged using an inductive coupling.

Furthermore, in one embodiment the guide indicia generation means 805 may comprise an I/O interface 1125 for the purposes of receiving input from the surgeon. The I/O interface 1125 is adapted not to compromise the protective cladding of the guide indicia generation means 805 and may therefore comprise a watertight pushbutton module for the purposes of receiving instructions from the surgeon. For example, the watertight pushbutton module may be operated a first time by the surgeon to power up the guide indicia generation means 805, operated a second time to select optimal alignment data for a first patient (and potential subsequent operational iterations for the purposes of selecting optimal alignment data for further patients), operated a third time to place the guide indicia generation means 805 in a data reception mode for the purposes of receiving the optimal alignment data across the wireless network 1130 and so on. Other I/O interfaces 1125 may be employed as opposed to a pushbutton module. For example, the stem 515 of the guide 500 may be twisted with respect to the guide indicia generation means 805, wherein each position of the stem with reference to the guide indicia generation means 805 corresponds to an operational mode of the guide indicia generation means.

Creating the Reference using a Guide Light Emission Means

Referring again to FIG. 5, it is apparent that the guide 500 comprises a guide light emission means 515*a*. As will become apparent from the description below, the guide light emission means 515*a* is adapted for the purposes of creating the reference once the guide 500 has been aligned correctly within the socket of the patient such that the reference may be used for the subsequent alignment of the implant cup 305. In a preferred embodiment, the light emission means 515 is detachable from the shaft 510 of the guide 500 so as to allow for the re-use of the guide light emission means 515*a* in the reference marker 920 or impactor 1005 as described below. The guide light emission means 515*a* preferably comprises a watertight and ruggedised cladding suited for a sterile operational environment.

Figure 9:
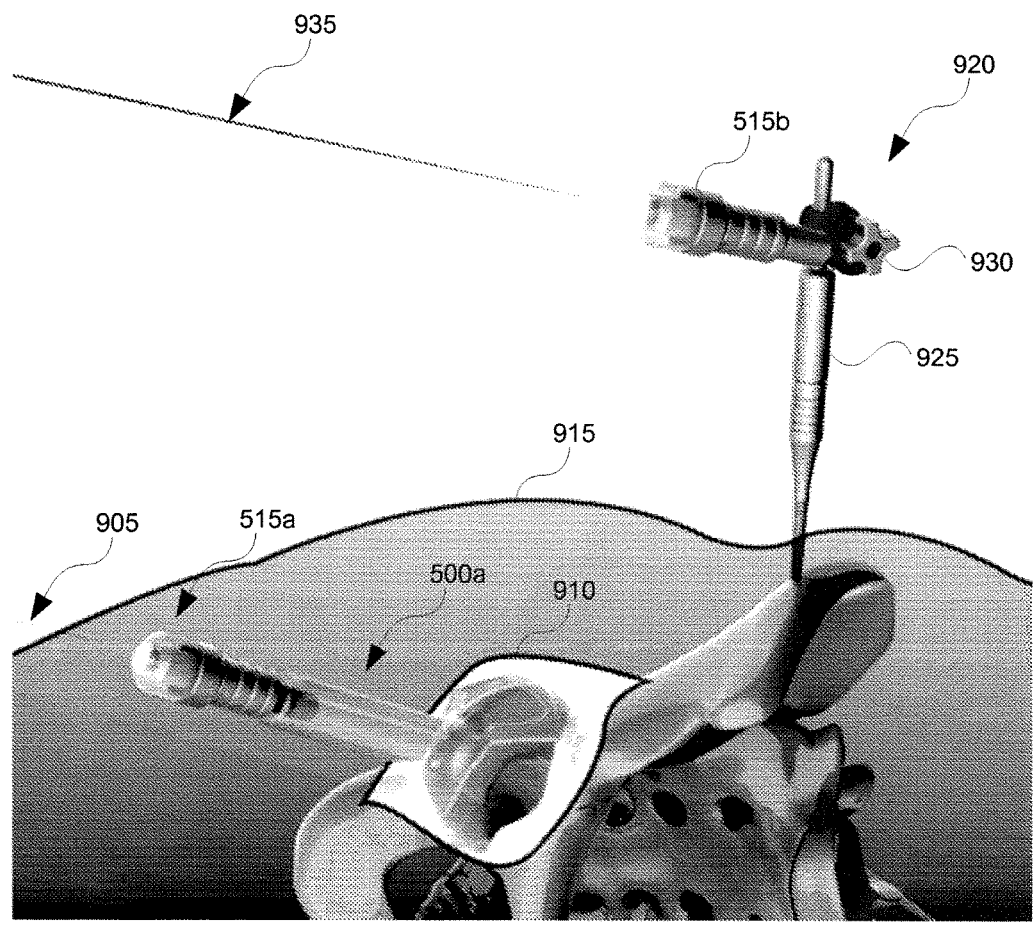
FIG. 9 shows the guide of FIG. 5 having been inserted into a socket so as to emit a guide light beam for creating a reference point and a reference marker similarly adapted for emitting a reference marker light beam for alignment with the reference point for aligning the reference marker in accordance with another preferred embodiment of the present invention.

The guide light emission means 515*a* is adapted to emit a guide reference light beam 905 for the purposes of creating the reference. Specifically, referring to FIG. 9, there is shown the guide 500 having been inserted into a socket. As is apparent, a wound 910 has been opened in the body 915 of the patient adjacent the socket (and acetabulum socket in this case) and the socket engaging portion 505*a* inserted into the socket so as to correctly aligned the guide 500. In this position, the guide light emission means 515*a* emits a guide reference light beam 905 for the purposes of creating the reference on a surface, such as the ceiling of an operating theatre.

In a preferred embodiment, the light emission means 515 is a laser emission means so as to provide an accurate pinpoint reference.

Fixing the Reference using a Reference Marker

Now, the reference having been created by the guide 500, the method 100 progresses to step 125 where the reference is fixed using a reference marker 920 aligned in accordance with the guide 500. The use of the reference marker 920 allows for the removal of the guide 500 for the subsequent insertion of the implant 305.

There are described herein two manners by which the reference marker 920 may be aligned in accordance with the guide 500.

In a first embodiment the reference marker 920 is aligned in accordance with the guide 500 without the use of a guide light emission means 515*a*. Specifically, in this embodiment, the reference marker 920 is adapted for physically referencing the guide 500. In this embodiment, reference marker 920 comprises a reference pin 925 and the guide 500 comprises a reference pin guide (not shown) adapted for allowing the surgeon to align the reference pin 925 using the reference pin guide. In one embodiment, the reference pin guide may comprise a sheath (not shown) adapted for receiving the reference pin 925 therethrough so as to allow the reference pin 925 to be driven into the pelvis of the patient. Alternatively, the sheath may be adapted for receipt of a drill bit for the purposes of drilling a drill hole for subsequent insertion of the reference pin 925. For embodiments where the referenced in 925 is located substantially distal from the guide 500, an outrigger (not shown) may be used for the purposes of aligning the reference pin 925 with reference to the guide 500.

In a second embodiment, the reference marker 920 similarly comprises a reference marker light emission means 515*b* adapted for fixing a reference. Specifically, the reference marker 920 is configured such that the reference marker light beam 935 from the reference marker light emission means 515*b* coincides substantially with the guide light beam 905 from the guide light emission means 515*a*. For example, where the guide 500 has been inserted into the socket such that the guide light emission means 515*b* emits a guide light beam 905, the reference marker 920 is configured such that the reference marker light beam 935 from the reference marker light emission means 515*b* coincides substantially with the guide light beam 905, generally within a tolerance of about 30 cm.

As is apparent from the embodiment, an additional wound has been created for the purposes of allowing the reference pin 925 to be fastened to the pelvis of the patient. Fastening the reference marker 925 to the pelvis of the patient will maintain the reference point should the position of the patient be adjusted during operation.

So as to assist in the alignment of the reference marker light beam 935 with the guide light beam 905, reference marker may comprise a joint 930. Once the reference pin 925 has been fastened to the pelvis bone, the joint 930 is manipulated so as to align the reference marker light beam 935 with the guide light beam 905. In one embodiment, the joint 930 is a uni axial joints wherein the vertical alignment of the reference marker light beam 935 is controlled by the joint 930 and the horizontal alignment of the reference marker light beam 935 is controlled by twisting the reference pin 925. However, in an alternative embodiment, the joint 930 is a poly-axial joint allowing both vertical and horizontal configuration.

Delivery of the Implant in Alignment with the Reference

Having fixed the reference using the reference marker 920, the method 100 progresses to step 130 where the implant 305 is delivered in alignment with the reference.

Figure 10:
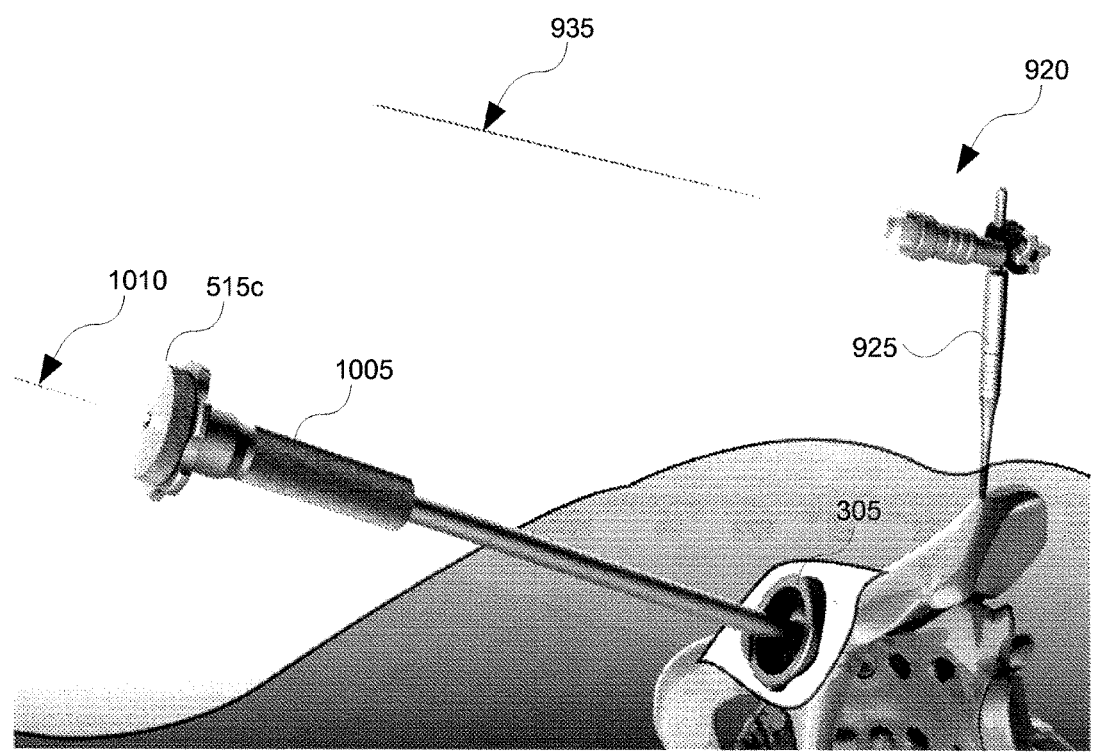
FIG. 10 shown the delivery of the implant cup using an impactor having an impactor light emission means adapted for emitting an impact light beam for alignment with the reference in accordance with another preferred embodiment of the present invention.

Specifically, referring to the embodiment given in FIG. 10, there is shown the delivery of the implant cup 305 using an impactor 1005. The impact 1005 is aligned in accordance with the reference so as to deliver the implant cup 305 in the optimal alignment.

Generally, prior to the delivery of the implant cup 305, the acetabulum is reamed so as to provide a suitable bedding for the implant cup 305.

There are two embodiments by which the impactor 1005 may be aligned in accordance with the reference. In a first embodiment, the impactor 1005 is adapted to physically engage the reference marker 920. Specifically, the impactor 1005 may be adapted to engage the reference pin 925 during impaction. There are a number of manners by which the impactor 1005 may engage the reference pin 925. Specifically, where the reference pin 925 is substantially proximal the acetabulum, the impactor 1005 may comprise a reference pin engagement (not shown) for the purposes of receiving the reference pin 925 therein. As such, in use, the surgeon would insert the reference pin 925 within the reference pin engagement of the impactor 1005. Where the reference pin 925 is located substantially distal the acetabulum, the impact 1005 may comprise a suitable outrigger to engage the reference pin.

In a second embodiment, the impactor 1005 comprises an impactor light emission means 515c adapted for emitting an impactor light beam 1010. As is apparent, the impactor light emission means 515c comprises a substantially flat head and ruggedised so as to be suited for percussion during the impaction process. In aligning the impactor 1005, the surgeon will align the impactor light beam 1010 with the reference marker light beam 935.

It should be noted that in one embodiment, the guide 500 may be adapted to conform to the geometric features surrounding the socket so as to negate the requirement for a reference marker 920. Specifically, in this embodiment, an optimal alignment may be calculated, and instead of employing the geometric features of the socket for aligning the guide 500 in accordance with the optimal alignment, the guide 500 may be manufactured or configured to conform to geometric features of the pelvis (or other bone) as opposed to those of the socket. In one manner, the guide 500 may be provided substantially adjacent the socket such that only one wound is required. In this manner, the guide 500 would allow for sufficient space for the insertion of the implant 305 using the impactor 1005. In another embodiment, a secondary wound may be opened so as to allow the guide 500 to engage a substantially distal geometric feature. Furthermore, in this embodiment, the guide 500 may comprise a fastening aperture so as to allow a fastener (such as a screw) to be employed to fastened the guide 500 to the geometric feature once the guide has been aligned correctly.

Interpretation
Wireless:

The invention may be embodied using devices conforming to other network standards and for other applications, including, for example other WLAN standards and other wireless standards. Applications that can be accommodated include IEEE 802.11 wireless LANs and links, and wireless Ethernet.

In the context of this document, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In the context of this document, the term "wired" and its derivatives may be used to describe circuits, devices, systems, methods, techniques, communications channels, etc., that may communicate data through the use of modulated electromagnetic radiation through a solid medium. The term does not imply that the associated devices are coupled by electrically conductive wires.

Processes:

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

Processor:

In a similar manner, the term "processor" may refer to any device or portion of a device that processes electronic data, e.g., from registers and/or memory to transform that electronic data into other electronic data that, e.g., may be stored in registers and/or memory. A "computer" or a "computing device" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. The processing system further may include a memory subsystem including main RAM and/or a static RAM, and/or ROM.

Computer-Readable Medium:

Furthermore, a computer-readable carrier medium may form, or be included in a computer program product. A computer program product can be stored on a computer usable carrier medium, the computer program product comprising a computer readable program means for causing a processor to perform a method as described herein.

Networked or Multiple Processors:

In alternative embodiments, the one or more processors operate as a standalone device or may be connected, e.g., networked to other processor(s), in a networked deployment, the one or more processors may operate in the capacity of a server or a client machine in server-client network environment, or as a peer machine in a peer-to-peer or distributed network environment. The one or more processors may form a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Additional Embodiments

Thus, one embodiment of each of the methods described herein is in the form of a computer-readable carrier medium carrying a set of instructions, e.g., a computer program that are for execution on one or more processors. Thus, as will be appreciated by those skilled in the art, embodiments of the present invention may be embodied as a method, an apparatus such as a special purpose apparatus, an apparatus such as a data processing system, or a computer-readable carrier medium. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

Carrier Medium:

The software may further be transmitted or received over a network via a network interface device. While the carrier medium is shown in an example embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media.

Implementation:

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Means for Carrying Out a Method or Function

Furthermore, some of the embodiments are described herein as a method or combination of elements of a method that can be implemented by a processor of a processor device, computer system, or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

Connected

Similarly, it is to be noticed that the term connected, when used in the claims, should not be interpreted as being limitative to direct connections only. Thus, the scope of the expression a device A connected to a device B should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other.

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the orthopaedic implant industries.

The invention claimed is:

1. A method for aligning an implant, the method comprising: providing a guide having a socket engaging portion configured in accordance with patient specific data and a light-emitting guide indicia generating means which is adapted for aligning the guide by creating a reference; engaging the socket engaging portion in a socket align the guide; creating a reference using the light-emitting guide indicia generating means; fastening a reference marker to a patient to define a reference point fixed to the patient, the reference marker comprising a reference marker light emission means adapted to emit from the reference point a reference marker light beam adapted for alignment with the reference; and aligning the implant accordance with the reference.

2. A method as claimed in claim 1, wherein the method further comprises manufacturing the socket engaging portion in accordance with the patient specific data.

3. method as claimed in claim 1, further comprising manufacturing the socket engaging portion in accordance with alignment data.

4. A method as claimed in claim 1, further comprising manufacturing the socket engaging portion in accordance with geometric features of the socket.

5. A method as claimed in claim 1, wherein the guide indicia generation means further comprises a guide indicia device adapted to display guide indicia, the guide indicia display device being configured in accordance with configuration data, wherein the configuration data comprises alignment data which comprises inclination and anteversion angle data, and the configuration data further comprising a geometric feature, of the socket.

6. A method as claimed in claim 5, wherein the guide indicia display device comprises a plurality of light modules.

7. A method as claimed in claim 6, wherein the guide indicia generation means is adapted to display the guide indicia in, on or adjacent to a surface of the guide indicia generation means using the plurality light models.

8. A method as claimed in claim 7, further comprising transmitting the configuration data to the guide indicia generation means by wired or wireless means.

9. A method as claimed in claim 1, further comprising calculating optimal alignment data in accordance with the patient specific data.

10. A method as claimed in claim 9, further comprising calculating candidate alignment data in accordance with the patient specific data and selecting the optimal alignment data from the candidate alignment data.

11. A method as claimed in claim 10, further comprising calculating the candidate alignment data in accordance with patient data and selecting the optimal alignment data in accordance with at least one desired post implant activity.

12. A method as claimed in claim 11, wherein the patient data comprises dynamic characteristic data representing at least one dynamic characteristic.

13. A method as claimed in claim 12, further comprising calculating the dynamic characteristic data from imaging data obtained from an imaging technique selected from the set of imaging techniques comprising CT and radiograph imaging techniques.

14. A method as claimed in claim 13, further comprising capturing the image data from a patient during at least one functional activity.

15. A method as claimed in claim 12, wherein the dynamic characteristics data comprises dynamic characteristic data selected from the set of characteristic data comprising lumber cobb angle, sacreal slope and anterior pelvic plane characteristic data.

16. A method as claimed in claim 12, further comprising calculating the dynamic characteristic data in accordance with a virtual model.

17. A method as claimed in claim 9, wherein calculating candidate alignment data comprises simulating at least one functional activity.

18. A method as claimed in claim 17, wherein calculating candidate alignment data further comprises simulating at least one alignment of the implant.

19. A method as claimed in claim 17, further comprises employing a rigid body dynamic physics simulation.

20. A method as claimed in claim 17, wherein calculating candidate alignment data comprises calculating at least one joint reaction vector from a simulation of a functional activity.

21. A method as claimed in claim 20, further comprising selecting the optimal alignment data in accordance the at least one joint reaction vector.

22. A method as claimed in claim 20, further comprising selecting the optimal alignment data utilising desired articulation or contact mechanics.

23. A method as claimed in claim 20, further comprising selecting the optimal alignment data in accordance with a desired post implant activity.

24. A method as claimed in claim 1, wherein creating the reference comprises projecting a guide reference light beam from the guide light emission means onto a surface and noting the location or the light beam on the surface.

25. A method as claimed in claim 24, wherein the guide light emission means is detachable.

26. A patient implant alignment system for alignment an implant comprising: a guide having a socket engaging portion configured in accordance with patient specific data and a light-emitting guide indicia generating means which is, adapted for aligning the guide by creating a reference; and a reference marker which is adapted for fastening to a patient to define a reference point fixed to the patient, the reference marker comprising a reference marker light emission means adapted to emit from the reference point, a reference marker light beam adapted for alignment with the reference.

27. A patient implant alignment system as claimed in claim 26, wherein the guide indicia generation means comprises: a processor for processing digital data; a memory device for storing digital data including computer program code and being coupled to the processor; and a guide indicia display device for displaying the guide indicia and being coupled to the processor, wherein processor is controlled by the computer program code to: display, using the guide indicia display device, the guide indicia in accordance with configuration data.

28. A patient implant alignment system as clamed in claim 27, wherein the configuration data comprises alignment data which comprises inclination and anteversion angle data, and wherein the configuration data comprises a geometric feature of the socket.

29. A patient implant alignment system as claimed in claim 27, further comprising a data interface receiving data from a data network and being coupled to the processor, wherein the processor is further controlled by the computer program code to receive, via the data interface, the configuration data.

30. A patient alignment system as claimed in claim 27, wherein the processor is further controlled by the computer program code to store, the memory device, the configuration data.

31. A patient implant alignment system as claimed in claim 26, further comprising computer program code instructions for generating the guide indicia for aligning the guide, computer program instructions comprising instructions for displaying, using a guide indicia display device, the guide indicia in accordance with configuration data.

32. A patient implant alignment system as claimed in claim 31, wherein configuration data comprises alignment data which comprises inclination and anteversion angle data, and wherein the configuration data comprises a geometric feature of the socket.

33. A patient implant alignment system as claimed in claim 31, further comprising instructions for receiving, via a data interface, the configuration data.

34. A patient implant alignment system as claimed in claim 31, further comprising instructions for storing, in the memory device the configuration data.

35. A patient implant alignment system as claimed in claim 26, wherein the socket engaging portion is manufactured in accordance with alignment data.

36. A patient implant alignment system as claimed in claim 26, wherein the socket engaging portion comprises a guide indicia generation means for generating a guide indicia for aligning the guide, the guide indicia generation means comprising a guide indicia display device adapted to display the guide indicia.

37. A patient implant alignment system as claimed in claim 36, wherein the guide indicia display device is configured in accordance with configuration data, wherein the configuration data comprises alignment data which comprises inclination and anteversion angle data, and wherein the configuration data comprises a geometric feature of the socket.

38. A patient implant alignment system as claimed in claim 37, wherein the guide indicia display device comprises a plurality of light modules.

39. A patient implant alignment system as claimed in claim 36, wherein the guide indicia, generation means comprises a wired or wireless receiver module adapted for receiving the configuration data.

40. A patient implant alignment system as claimed in claim 26, further comprising an impactor for aliening an implant into socket in alignment with a reference fixed by the reference marker.

41. A patient implant alignment system as claimed in claim 40, wherein the impactor is adapted to engage the reference marker.

42. A patient implant alignment system as claimed in claim 41, wherein the impactor comprises an impactor light emission means adapted for emitting an impactor light beam adapted for alignment with the reference.

43. A method as claimed in claim 24, wherein the guide light emission means is adapted to emit a second guide reference light beam.

44. A method as claimed in claim 1, wherein aligning the implant comprises delivering the implant into a socket with an impactor aligned in accordance with the reference.

* * * * *